(12) United States Patent
Luppi

(10) Patent No.: US 6,779,523 B2
(45) Date of Patent: Aug. 24, 2004

(54) DEVICE FOR ARTIFICIAL RESPIRATION WITHOUT THE AID OF MASKS, PARTICULARLY FOR NEONATES AND PREMATURE INFANTS

(75) Inventor: Libero Luppi, Mirandola (IT)

(73) Assignee: Starmed S.p.A., Mirandola (IT)

( * ) Notice: Subject to any disclaimer, the term of this patent is extended or adjusted under 35 U.S.C. 154(b) by 0 days.

(21) Appl. No.: 10/461,477

(22) Filed: Jun. 16, 2003

(65) Prior Publication Data

US 2004/0007233 A1 Jan. 15, 2004

(30) Foreign Application Priority Data

Jul. 9, 2002 (IT) .......................................... MI02A1502

(51) Int. Cl.[7] .............................................. A61G 10/00
(52) U.S. Cl. .............................. 128/205.26; 128/202.12
(58) Field of Search ....................... 128/201.22, 201.23, 128/201.28, 201.29, 202.12, 202.18, 204.18, 205.26; 600/21, 22

(56) References Cited

U.S. PATENT DOCUMENTS 2,700,384 A * 1/1955 Ivory .................... 128/202.16
2,822,803 A * 2/1958 Huxley, III et al. .......... 601/43
3,903,869 A * 9/1975 Bancalari ................ 128/202.12
3,993,042 A * 11/1976 Gatts ............................ 600/22
4,003,378 A * 1/1977 Pickering ................ 128/205.17
4,481,938 A   11/1984 Lindley
4,832,042 A * 5/1989 Poppendiek et al. ......... 600/543
4,926,844 A * 5/1990 Lindley ....................... 601/43
4,949,714 A * 8/1990 Orr ........................ 128/200.24
5,582,574 A * 12/1996 Cramer ........................ 600/21
5,832,919 A * 11/1998 Kano et al. ............. 128/205.26

FOREIGN PATENT DOCUMENTS

EP   0 687 456   12/1995
FR   1 136 521    5/1957

* cited by examiner

Primary Examiner—Henry Bennett
Assistant Examiner—Teena Mitchell
(74) Attorney, Agent, or Firm—Guido Modiano; Albert Josif; Daniel O'Byrne

(57) ABSTRACT

A device for artificial respiration without the aid of masks, particularly for neonates and premature infants, comprising a frame that is provided with a first environment for accommodating the head of a patient and with a second environment that forms a resting surface for the back of the patient, the first and second environments being separated hermetically, and the first environment being sealed hermetically and being provided with at least one port for connection to a ventilation unit, the second environment further containing an abutment surface that can be arranged according to the length of the trunk of the patient.

7 Claims, 2 Drawing Sheets

DEVICE FOR ARTIFICIAL RESPIRATION WITHOUT THE AID OF MASKS, PARTICULARLY FOR NEONATES AND PREMATURE INFANTS

BACKGROUND OF THE INVENTION

The present invention relates to a device for artificial respiration without the aid of masks, particularly for neonates and premature infants.

As is known, hoods for artificial respiration without the aid of masks are already known which can be applied at the head of the patient and are structured so as to provide in practice a seal around the neck of the patient. Moreover, in order to keep the hood stably in position, straps or the like are used which engage under the armpits of the patient.

This type of solution has proved to be particularly valid in the case of adult patients but is not applicable to neonates or premature infants, since it is inconceivable to be able to provide a seal by means of an elastic membrane around the neck of the patient and it is also not possible to connect the hood by means of straps that engage under the armpits of the neonate.

Accordingly, up to now it has not been possible to perform artificial respiration in neonates and premature infants except by resorting to the conventional applications of masks or of intubated devices.

SUMMARY OF THE INVENTION

The aim of the invention is to solve the problem described above, by providing a device for artificial respiration without the aid of masks that allows to perform the treatment on a neonate, allowing to create pressurized ventilation conditions without applying masks or the like.

Within this aim, an object of the invention is to provide a device in which it is possible to perform both respiration processes and to provide hermetic seals without thereby causing any discomfort to the patient, who remains in a "natural" posture without being subjected to stresses of any kind.

Another object of the present invention is to provide a device that thanks to its particular constructive characteristics is capable of giving the greatest assurances of reliability and safety in use.

Another object of the present invention is to provide a device for artificial respiration without the aid of masks, particularly for neonates and premature infants, that can be obtained easily starting from commonly commercially available elements and materials and is further competitive from a merely economical standpoint.

This aim and these and other objects that will become better apparent hereinafter are achieved by a device for artificial respiration without the aid of masks, particularly for neonates and premature infants, according to the invention, characterized in that it comprises a frame that is provided with a first environment for accommodating the head of a patient and with a second environment that forms a resting surface for the back of the patient, said environments being separable hermetically, said first environment being sealable hermetically and being provided with at least one port for connection to a ventilation unit, said second environment containing an abutment surface that can be arranged according to the length of the trunk of the patient.

BRIEF DESCRIPTION OF THE DRAWINGS

Further characteristics and advantages of the invention will become better apparent from the description of a preferred but not exclusive embodiment of a device for artificial respiration without the aid of masks, particularly for neonates and premature infants, illustrated by way of non-limitative example in the accompanying drawings, wherein.

DESCRIPTION OF THE PREFERRED EMBODIMENTS

Figure 1:
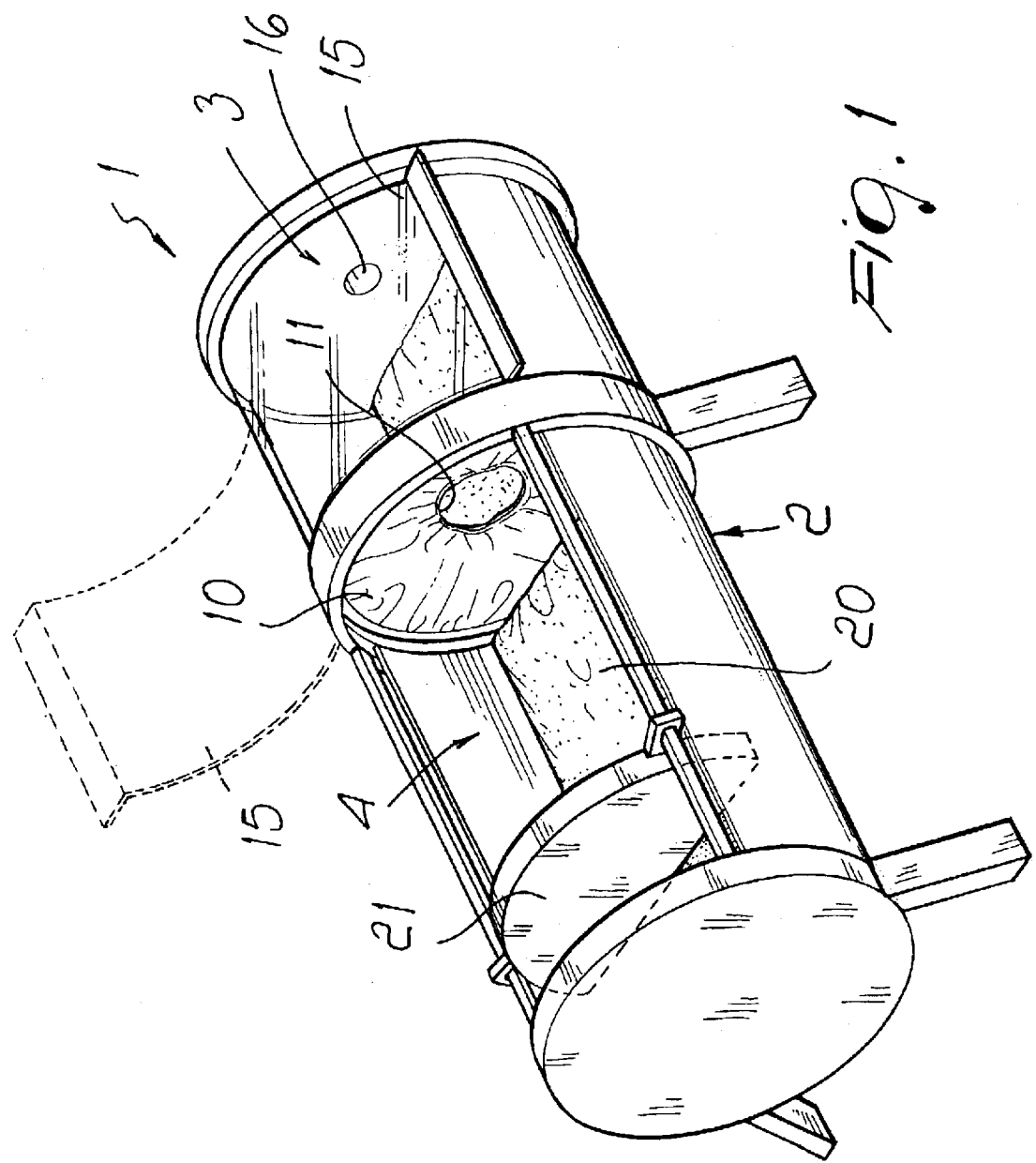
FIG. 1 is a schematic perspective view of the device.
Figure 2:
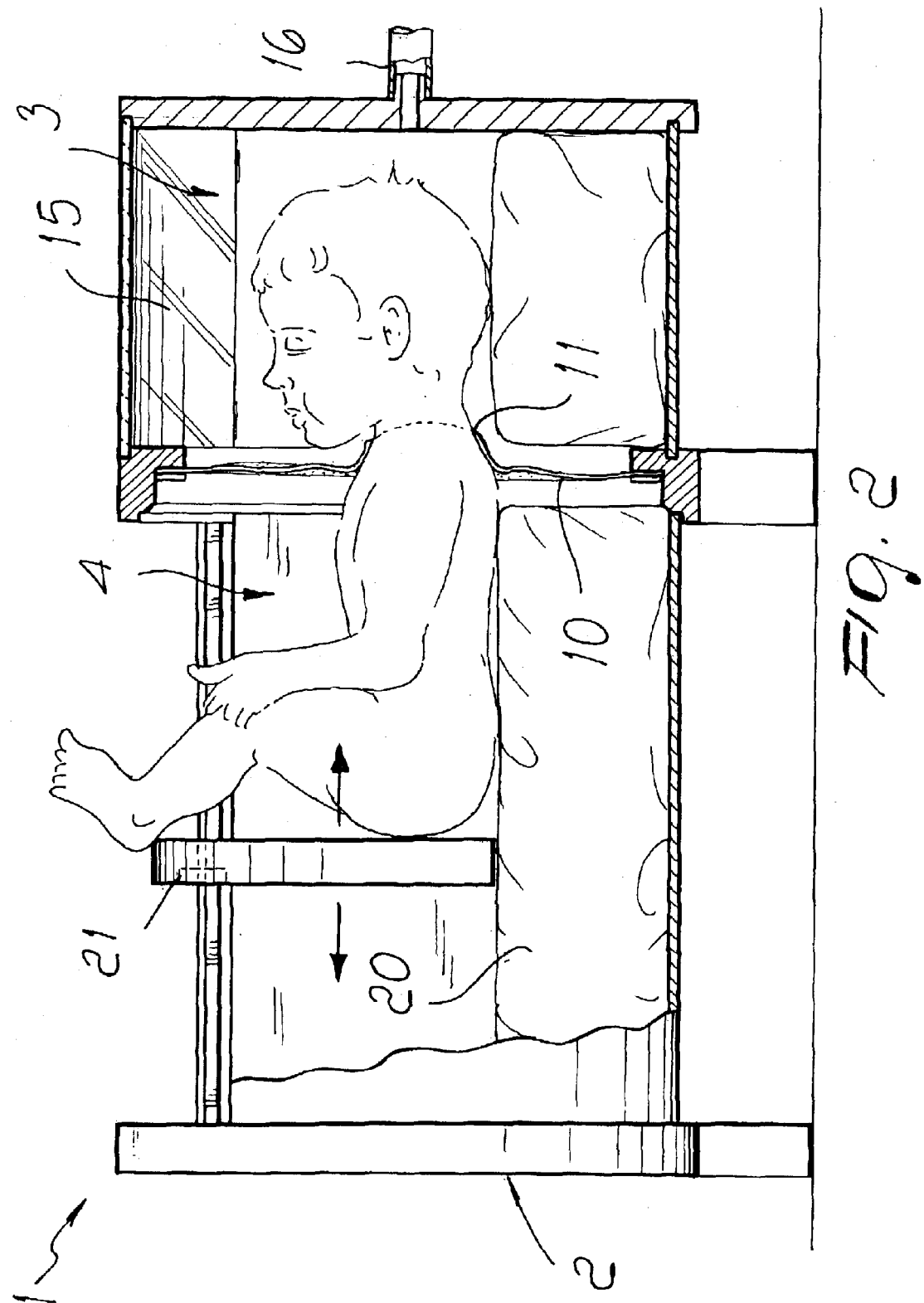
FIG. 2 is a sectional view of the device.

With reference to the figures, the device for artificial respiration without the aid of masks, particularly for neonates and premature infants, according to the invention, generally designated by the reference numeral 1, comprises a supporting frame 2, which forms a first environment 3 for accommodating the head of a patient and a second environment 4 for accommodating the trunk of the patient.

The first environment 3 and the second environment 4 are hermetically separable by means of a membrane 10 made of elastically flexible material, which preferably has a frusto-conical shape with a central hole 11 whose diameter is larger than the diameter of the neck of the patient, so as to not constrict the patient at the level of the neck, this being particularly important in the case of neonates.

The first environment 3 can be closed hermetically with respect to the outside by means of a door 15 or other elements and is provided with a port, generally designated by the reference numeral 16, for connection to a ventilation unit.

Furthermore, at the first environment there can be different kinds of accesses for inspection and servicing that can be used according to the contingent requirements.

A first important feature of the invention consists in that the membrane 10, when a given pressure occurs within the first environment 3, is suitable to form a seal by resting on the base of the neck and on the shoulders of the patient, thus obtaining an optimum seal of the first environment without however causing any stress to the patient.

The second environment 4 is provided with a surface 20 for supporting the back of the infant and there is also an abutment surface 21 that can slide so that it is positioned according to the length of the trunk of the patient.

Substantially, the surface 21 rests against the base of the back of the patient in order to be able to compensate for the thrust applied by the pressure in the environment 3.

This effect can be achieved without having to resort to straps or similar elements that might damage the particularly delicate skin of the neonate.

It should be added to the above that the second environment 4 can be closed hermetically so as to provide, if required, a negative pressure around the body of the patient, so as to facilitate ribcage expansion.

From the above description it is evident that the invention achieves the intended aim and objects and in particular the fact is stressed that the device described above allows to pressurize the airways, forming a hermetic environment by means of an extremely pliable membrane which, in use, causes absolutely no traumas of any kind to the patient and further allows, by having a pressurized environment, to pressurize the pulmonary alveoli.

Furthermore, the constructive simplicity of the assembly allows to accommodate the patient, usually a neonate, in a natural position, achieving retention in position thanks to the abutment surface, which can be arranged at the selected point.

The invention thus conceived is susceptible of numerous modifications and variations, all of which are within the scope of the appended claims.

All the details may further be replaced with other technically equivalent elements.

In practice, the materials used, so long as they are compatible with the specific use, as well as the dimensions and the contingent shapes, may be any according to requirements.

The disclosures in Italian Patent Application No. MI2002A001502 from which this application claims priority are incorporated herein by reference.

What is claimed is:

1. A device for artificial respiration without the aid of masks, particularly for neonates and premature infants, comprising a frame that is provided with a first environment for accommodating the head of a patient and with a second environment that forms a resting surface for the back of the patient, said environments being separable hermetically, said first environment being sealable hermetically and being provided with at least one port for connection to a ventilation unit, said second environment containing a sliding abutment surface that can be positioned according to the length of the trunk of the patient so as to compensate for a thrust applied by pressure in said first environment.

2. The device according to claim 1, further comprising, between said first environment and said second environment, a membrane made of elastically flexible material which has a central hole whose diameter is equal to, or greater than, the diameter of the neck of the patient.

3. The device according to claim 2, wherein said membrane is substantially frustoconical.

4. The device according to claim 1, wherein said first environment comprises a door that can be opened and closed hermetically.

5. The device according to claim 2, wherein said membrane forms a seal by resting on the base of the neck and on the shoulders of the patient.

6. The device according to claim 1, wherein said abutment surface can slide parallel to the length of the back of the patient and can be locked in the selected position.

7. The device according to claim 1, wherein said second environment can be closed hermetically in order to provide a negative pressure around the trunk of the patient, said pressure being adapted to facilitate ribcage expansion.

* * * * *